(12) United States Patent
Gellert

(10) Patent No.: US 9,546,972 B2
(45) Date of Patent: Jan. 17, 2017

(54) THERMAL CONDUCTIVITY DETECTOR

(71) Applicant: Siemens Aktiengesellschaft, Munich (DE)

(72) Inventor: Udo Gellert, Bellheim (DE)

(73) Assignee: Siemens Aktiengesellschaft, Munich (DE)

( * ) Notice: Subject to any disclaimer, the term of this patent is extended or adjusted under 35 U.S.C. 154(b) by 83 days.

(21) Appl. No.: 14/604,954

(22) Filed: Jan. 26, 2015

(65) Prior Publication Data
US 2015/0219578 A1  Aug. 6, 2015

(30) Foreign Application Priority Data

Jan. 27, 2014  (EP) .................................... 14152706

(51) Int. Cl.
*G01N 27/18* (2006.01)
*G01N 30/66* (2006.01)

(52) U.S. Cl.
CPC ............. *G01N 27/18* (2013.01); *G01N 30/66* (2013.01)

(58) Field of Classification Search
CPC ...................................................... G01N 25/18
USPC .................................. 73/25.01, 25.03, 25.05
See application file for complete search history.

(56) References Cited

U.S. PATENT DOCUMENTS

| | | | | |
|---|---|---|---|---|
| 2,512,857 A * | 6/1950 | Gow | .................. | G01N 27/18 73/25.03 |
| 3,474,660 A * | 10/1969 | Dooley | .................. | G01N 27/18 73/25.03 |
| 7,021,821 B2 | 4/2006 | Bonne | | |
| 8,066,429 B2 * | 11/2011 | Danley | .................. | G01K 17/00 374/10 |
| 2004/0136435 A1 | 7/2004 | Gellert | | |
| 2005/0265422 A1 * | 12/2005 | Bonne | .................. | G01N 25/18 374/44 |
| 2010/0242573 A1 * | 9/2010 | Matsuhama | .......... | G01N 25/18 73/25.03 |
| 2012/0111854 A1 * | 5/2012 | Gaspard | ............... | H05B 6/1209 219/650 |
| 2015/0052974 A1 * | 2/2015 | Pieczarek | .............. | G01N 25/18 73/25.03 |

FOREIGN PATENT DOCUMENTS

| | | |
|---|---|---|
| CN | 2289242 | 8/1998 |
| CN | 102183605 | 9/2011 |
| DE | 10318450 B3 | 7/2004 |
| DE | 102009014618 A1 | 8/2010 |
| EP | 1921443 A1 | 5/2008 |
| GE | DE 10119788 A1 * | 7/2004 |
| JP | 2001337058 A | 12/2001 |
| WO | WO 2005/119232 | 12/2005 |

* cited by examiner

*Primary Examiner* — Michael A Lyons
*Assistant Examiner* — Hoang Nguyen
(74) *Attorney, Agent, or Firm* — Cozen O'Connor

(57) ABSTRACT

A thermal conductivity detector includes at least four detector components that are arranged in receptacles of a thermal conduction block in a circle around a center axis of the thermal conduction block. The thermal conduction block comprises a central portion along the axis, the cross-axial dimensions of the central portion being less than the diameter of the circle. There are at least four equal peripheral portions that are connected solely to the central portion and are separated from each other, each of the peripheral portions carrying one of the detector components.

7 Claims, 2 Drawing Sheets

THERMAL CONDUCTIVITY DETECTOR

BACKGROUND OF THE INVENTION

1. Field of the Invention

The present application generally relates to a thermal conductivity detector comprising at least four detector components arranged in receptacles of a thermal conduction block in a circle around a center axis of the thermal conduction block.

2. Related Art

Thermal conductivity detectors, such as those disclosed in U.S. Pat. No. 2,512,857, U.S. Pat. No. 3,474,660 or DE 103 18 450 B3, are used to detect certain liquid or gaseous substances (fluids) on the basis of their characteristic thermal conductivity, particularly in gas chromatography. To that end, the substances to be detected are successively guided past an electrically heated filament disposed in a channel, after their chromatographic separation. Depending on the thermal conductivity of the substance flowing past, more or less heat is diverted from the heating filament to the channel wall, and the heating filament is correspondingly cooled to a greater or lesser degree. As a result of the cooling of the heating filament, its electrical resistance changes, which can be detected. For this purpose, the heating filament is typically placed in a measuring bridge, which contains additional resistors and an additional heating filament in a further channel through which a reference fluid flows. Instead of the resistors, further filaments may be provided that are fluidically parallel or in series with the filaments in the measurement channel and the reference channel, respectively. In the latter, the heating filaments and the surrounding channels are referred to individually as detector components, and collectively as the thermal conductivity detector.

To keep the detector components on the same temperature level, it is known from the above-mentioned references to have the detector components accommodated in a thermal conduction block that is made of a suitable heat conducting material such as brass or aluminum. For the same reason, the design of the thermal conductivity detector is thermally symmetrical with the detector components being arranged in a circle around a center axis of the thermal conduction block.

The detection limit of the thermal conductivity detector may be limited by thermal crosstalk between the detector components. For example, when a chromatographically separated gas fraction with a high thermal conductivity flows past the heating filament in the measurement channel and the carrier gas passing the heating filament in the reference channel has a lower thermal conductivity, the heat flows from the filaments to the respective channel walls. Accordingly, the wall temperatures will be different. Having different wall temperatures creates a temporary temperature imbalance within the thermal conduction block that affects the detector components differently. The thermal symmetry of the known thermal conductivity detectors is not good enough to compensate for this effect.

SUMMARY OF THE INVENTION

It is therefore an object of an embodiment of the present disclosure to provide a solution for the foregoing problem and to provide a thermal conductivity detector with an improved detection limit.

In one aspect, the application is related to a thermal conductivity detector comprising at least four detector components arranged in receptacles of a thermal conduction block in a circle around a center axis of the thermal conduction block. The thermal conduction block comprises a rotationally symmetric central portion along the axis, the cross-axial dimensions of the central portion being less than the diameter of the circle. There are at least four equal peripheral portions that are arranged symmetrically about the circle and are connected to the central portion with good thermal coupling. In addition, the peripheral portions are separated from each other. Each of the peripheral portions carry one of the detector components.

Since the portions of the thermal conduction block that carry the detector components are thermally connected only via the central portion, the thermal path length or distance is the same between all detector components such that thermal crosstalk coming from any detector component affects each of the other detector components in the same way and can thus be easily compensated if (for example) one of the other detector components measures a reference gas.

In one embodiment, the thermal conduction block may be formed in one part by e.g. casting, forming, or cutting. That means that the peripheral portions are formed integrally with the central portion. To achieve the mutual thermal isolation of the peripheral portions, the thermal conduction block may have notches, indentations, grooves, recesses or the like that extend from the outside inwards up to the central portion and completely axially through the thermal conduction block.

In an alternative embodiment, the thermal conduction block is formed in several parts comprising the peripheral portions that arranged around and in contact with the central portion. All usual types of connection, such as welding, brazing, bonding, screwing, plugging, etc., are possible as long as they provide a good thermal coupling of the peripheral portions to the central portion. In one embodiment, the peripheral portions may be separated from each other by spacers with low thermal conductivity to provide equal spacing between all neighboring peripheral portions and to improve the overall stability of the multi-part thermal conduction block.

Variations of the ambient temperature, in particular heat waves that emanate from an oven of a gas chromatograph, may affect not only the detector components but also the gases or liquids in the conduits to and from the detector components. In order to prevent the fluids from being differently affected by such temperature variations, at least the inlet conduits are formed by or installed in bores axially extending through the thermal conduction block. Thus the inlet conduits and, if applicable, the outlet conduits are in the same thermal symmetry as the detector components.

In one embodiment, to further improve the evenness of the heat distribution, the peripheral portions each may comprise a lower part and an upper part that, when mounted together, form a cavity between them as the receptacle for the detector component. The receptacles may be filled with a thermal paste.

The above mentioned heat waves may come from different directions and meet the thermal conductivity detector at different sides. Accordingly, in one embodiment, the central portion, at one or preferably both ends, projects axially beyond the peripheral portions and is connected to a heat conducting housing that at least partially encloses the central portion and the peripheral portions. Thus, the heat is transferred via the wall of the housing into the central portion, from where it propagates to the peripheral portions along same thermal paths.

BRIEF DESCRIPTION OF THE DRAWINGS

Aspects of the invention will now be described by way of example and with reference to the accompanying drawing, in which.

DETAILED DESCRIPTION OF THE PRESENTLY PREFERRED EMBODIMENTS

Figure 1:
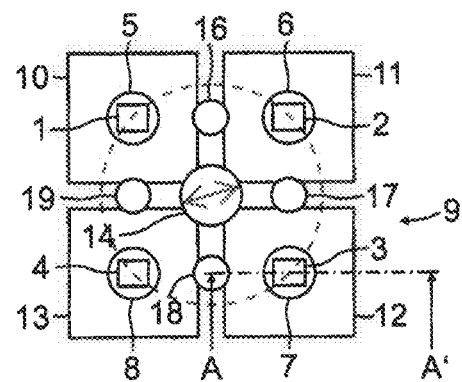
FIG. 1 is a plan view of an exemplary embodiment of the thermal conductivity detector.
Figure 2:
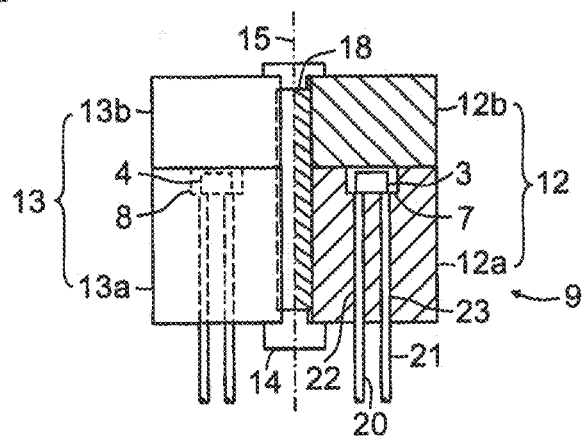
FIG. 2 is a side view of a modified version of the embodiment shown in FIG. 1 with a partial cross sectional view taken along line A-A'.

The thermal conductivity detector shown in FIGS. 1 and 2 comprises four detector components 1, 2, 3, 4, which are accommodated in receptacles 5, 6, 7, 8 formed on the top side of a thermal conduction block 9. The thermal conduction block includes several parts and comprises four peripheral portions 10, 11, 12, 13 arranged around and in contact with a central portion 14. All portions 10-14 are made of a highly heat-conductive material such as brass, copper or aluminum.

In the shown example, the peripheral portions 10-13 each have a rectangular cross section and the central portion 14 has a circular cross section. Generally, the portions of the thermal conduction block 9 can be of any cross section as long as the peripheral portions 10-13 are equal and the central portion 14 is n-fold, here n=°4, rotationally symmetrical. Accordingly, the receptacles 5-8 and the detector components 1-4 contained therein are situated in a circle around a center axis 15 of the thermal conduction block 9. The diameter of this circle is substantially larger than the cross-axial dimensions of the central portion 14.

In various embodiments, the peripheral portions 10-13 can be joined to the central portion 14 in different ways such as by welding, brazing, bonding, screwing or plugging to provide a good thermal coupling and heat transfer.

With the exception of their thermal contact to the central portion 14, the peripheral portions 10-13 are separated and are thus thermally isolated from each other. In various embodiments, spacers 16, 17, 18, and 19 are made of plastic or ceramic material with low thermal conductivity and provide equal spacing between all neighboring peripheral portions 10-13, as well as improve the overall mechanical stability of the multi-part thermal conduction block 9.

As illustrated in FIG. 2, using detector component 3 as an example, each of the detector components 1-4 is connected to an inlet conduit 20 and an outlet conduit 21 for a fluid to be measured. The conduits 20, 21 are installed in bores 22, 23 that axially extend through the thermal conduction block 9. The embodiment of FIG. 2 is different compared to that of FIG. 1 in that the peripheral portions 10-13 (of which only two (12, 13) are illustrated), each comprise a lower part 12a, 13a, and an upper part 12b, 13b, which, when mounted together, form a cavity between them as receptacle 7, 8 for the detector component 3, 4.

As illustrated in FIG. 1, the thermal path from each one of the detector components 1-4 to each other detector component leads through the central portion 14. The thermal path length is the same between all detector components 1-4 such that thermal crosstalk coming from any detector component affects each of the other detector components the same way and can therefore be easily compensated if, for example, one of the other detector components measures a reference gas.

Figure 3:
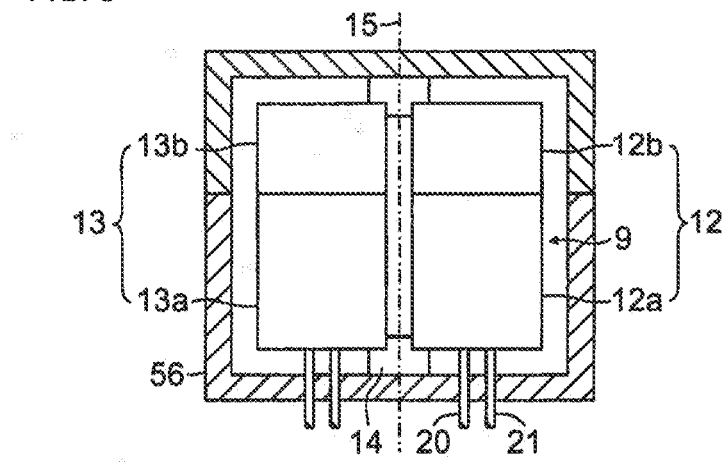
FIG. 3 is a view of the thermal conductivity detector of FIG. 2 with a housing and FIG. 4 is a plan view of another embodiment of the present invention.

FIG. 3 illustrates an exemplary thermal conductivity detector with the thermal conduction block 9 axially symmetrically arranged in a heat conducting housing 56. The central portion 14 projects at both ends axially beyond the peripheral portions 10-13 and is connected to the inner wall of the housing 56.

Figure 4:
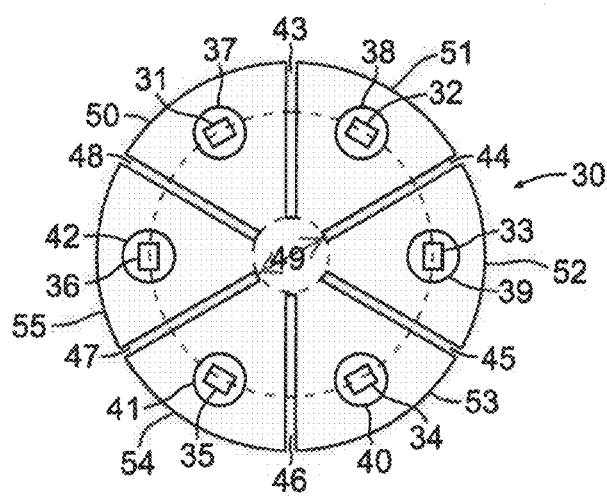

FIG. 4 is a plan view of another embodiment, where the thermal conduction block 30 is formed in one part by e.g., casting, forming, or cutting. The thermal conductivity detector comprises six detector components 31-36 that are accommodated in receptacles 37-42 formed on the top side of the thermal conduction block 30. In this example, the mainly cylindrical thermal conduction block 30 has six notches, indentations, grooves or recesses 43-48 that extend from the outside inwards up to the central portion 49 and completely axially through the thermal conduction block 30, thus forming and mechanically and thermally separating the peripheral portions 50-55.

In one aspect, the thermal conductivity detector may be used in a gas chromatograph wherein a sample of a gas mixture to be analyzed is conveyed by a carrier gas through a chromatographic separating device. Because of different migration rates through the separating device, the individual components of the gas mixture reach the output of the separating device at different times and are successively detected there by preferably two of the detector components 1-4 of the thermal conductivity detector. The detector components 1-4 may be micro-machined devices with heated filaments along the axis of a tubular channel, as generally known from, e.g., DE 10 2009 014618 A1 or US 2004/136435 A1. The filaments of the two detector components, e.g., 1 and 3, are diagonally arranged in a Wheatstone bridge together with the filaments of the other detector components, e.g., 2 and 4, through which, at the time of the detection, the carrier gas flows.

Thus, while there have been shown and described and pointed out fundamental novel features of the application as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A thermal conductivity detector comprising:
   a thermal conduction block having receptacles, a center axis, and a circle around the center axis; and
   at least four detector components arranged in the receptacles of the thermal conduction block in the circle around the center axis of the thermal conduction block, wherein the thermal conduction block comprises:
   a rotationally symmetric central portion along the axis, cross-axial dimensions of the central portion being less than the diameter of the circle; and
   at least four equal peripheral portions that are arranged symmetrically about the circle, connected to the central portion with good thermal coupling, and are separated from each other;

wherein each of the peripheral portions carries one of the detector components.

2. The thermal conductivity detector of claim 1, wherein the peripheral portions are formed integrally with the central portion.

3. The thermal conductivity detector of claim 2, wherein the integrally formed thermal conduction block includes at least one of notches, indentations, grooves, and recesses extending from the outside inwards up to the central portion and completely axially through the thermal conduction block.

4. The thermal conductivity detector of claim 1, wherein the thermal conduction block includes several parts comprising the peripheral portions arranged around and in contact with the central portion.

5. The thermal conductivity detector of claim 4, wherein the peripheral portions are separated from each other by spacers having a thermal conductivity whist is lower than a thermal conductivity of the thermal conduction block.

6. The thermal conductivity detector of claim 1, wherein:
each of the detector components is connected to an inlet conduit and an outlet conduit configured to measure a fluid; and
at least the inlet conduits are formed by or installed in bores axially extending through the thermal conduction block.

7. The thermal conductivity detector of claim 5, wherein:
each of the detector components is connected to an inlet conduit and an outlet conduit configured to measure a fluid; and
at least the inlet conduits are formed by or instilled in bores axially extending through the thermal conduction block.

\* \* \* \* \*